United States Patent
Sakamoto

(10) Patent No.: US 7,955,256 B2
(45) Date of Patent: Jun. 7, 2011

(54) LARYNGOSCOPE BLADE

(75) Inventor: Carl Kaoru Sakamoto, North Oaks, MN (US)

(73) Assignee: Carl Kaoru Sakamoto, North Oaks, MN (US)

( * ) Notice: Subject to any disclaimer, the term of this patent is extended or adjusted under 35 U.S.C. 154(b) by 989 days.

(21) Appl. No.: 11/462,442

(22) Filed: Aug. 4, 2006

(65) Prior Publication Data

US 2008/0033249 A1  Feb. 7, 2008

(51) Int. Cl.
- A61B 1/267 (2006.01)
- A61B 1/00 (2006.01)
- A61B 1/04 (2006.01)
- A61B 1/32 (2006.01)

(52) U.S. Cl. .......... 600/190; 600/120; 600/210; 600/239

(58) Field of Classification Search .......... 600/185–199, 600/120, 210, 239, 240; 128/860
See application file for complete search history.

(56) References Cited

U.S. PATENT DOCUMENTS

| | | | |
|---|---|---|---|
| 2,436,989 A * | 3/1948 | Daniels, Sr. ............ | 606/110 |
| 4,086,919 A * | 5/1978 | Bullard .................. | 600/188 |
| 4,112,933 A | 9/1978 | Moses | |
| 4,213,451 A * | 7/1980 | Swenson ............... | 600/215 |
| 4,314,551 A | 2/1982 | Kadell | |
| 4,360,008 A | 11/1982 | Corazzelli, Jr. | |
| 4,573,451 A | 3/1986 | Bauman | |
| 4,583,527 A * | 4/1986 | Musicant et al. ....... | 600/195 |
| 4,611,579 A | 9/1986 | Bellhouse | |
| 4,705,024 A | 11/1987 | Bainton | |
| 4,827,910 A * | 5/1989 | Mathews, III ......... | 600/194 |
| 4,924,855 A | 5/1990 | Salerno et al. | |
| 4,947,829 A * | 8/1990 | Bullard ................. | 600/101 |
| 4,947,896 A | 8/1990 | Bartlett | |
| D312,308 S | 11/1990 | Abadir | |
| D312,500 S | 11/1990 | Abadir | |
| 5,003,962 A | 4/1991 | Choi | |
| 5,036,835 A | 8/1991 | Filli | |
| 5,063,907 A | 11/1991 | Musicant et al. | |
| 5,498,231 A | 3/1996 | Franicevic | |
| 5,553,627 A * | 9/1996 | Newkirk ............... | 128/860 |
| 5,575,758 A * | 11/1996 | Easterbrook, III ..... | 600/193 |
| 5,584,795 A | 12/1996 | Valenti | |
| 5,776,053 A | 7/1998 | Dragisic et al. | |
| 5,938,591 A | 8/1999 | Minson | |
| D413,977 S | 9/1999 | Cranton et al. | |
| 5,984,863 A | 11/1999 | Ansari | |
| 5,993,383 A * | 11/1999 | Haase ................... | 600/191 |
| 6,053,166 A * | 4/2000 | Gomez ................. | 128/200.26 |
| 6,095,972 A | 8/2000 | Sakamoto | |
| 6,139,491 A | 10/2000 | Heine et al. | |
| 6,217,514 B1 | 4/2001 | Gruen et al. | |
| 6,231,505 B1 | 5/2001 | Martin | |
| 6,425,859 B1 * | 7/2002 | Foley et al. ............ | 600/204 |
| RE37,861 E * | 9/2002 | Schneider ............. | 600/199 |
| 6,494,828 B1 | 12/2002 | Berall | |
| 6,623,425 B2 | 9/2003 | Cartledge et al. | |
| 6,666,819 B2 | 12/2003 | Heine et al. | |
| 6,991,604 B2 * | 1/2006 | Cantrell ................. | 600/194 |
| 7,108,698 B2 * | 9/2006 | Robbins et al. ........ | 606/90 |
| 7,744,529 B2 * | 6/2010 | Sakamoto ............. | 600/190 |
| 2004/0034281 A1 | 2/2004 | Cartledge et al. | |
| 2004/0215062 A1 | 10/2004 | Dalle et al. | |

* cited by examiner

*Primary Examiner* — Linda C Dvorak
*Assistant Examiner* — Alireza Nia

(57) ABSTRACT

A laryngoscope blade is provided. The blade includes a base, a relatively straight main blade portion and a distal tip. The relatively straight main blade portion has a length that extends from the base. The distal tip has a length that extends from the main blade portion. The distal tip further has a width that extends out beyond the width of the main blade in a select direction. The distal tip further yet has a bend at a select location about its length.

20 Claims, 5 Drawing Sheets

LARYNGOSCOPE BLADE

BACKGROUND

A laryngoscope is a medical device that is used to position an endotracheal tube into a patient's trachea. In particular, a laryngoscope is used to expose a patient's aditus of the larynx thereby allowing the insertion of an endotracheal tube past the patient's vocal cords and into the patient's trachea. The insertion of an endotracheal tube provides an airway for ventilation and prevents foreign substances from entering the patient's trachea and lungs.

Two types of laryngoscopes are traditionally used by practitioners. The first type is generally called a MacIntosh blade. A MacIntosh blade is curved along its length and has a straight distal tip that is adapted to move the entire connecting tissue superior to the epiglottis of a patient to expose the aditus of the larynx. The second type of laryngoscope is generally called the Miller blade. The Miller blade is generally straight along its length and has a curved distal tip that is adapted to engage the epiglottis to expose the aditus of the larynx. The type of blade used depends on both the patient's anatomy and the preference of the practitioner. Accordingly, hospitals typically stock both types of blades in various sizes.

For the reasons stated above and for other reasons stated below which will become apparent to those skilled in the art upon reading and understanding the present specification, there is a need in the art for a multipurpose blade that is more effective and versatile than traditional blades.

SUMMARY OF INVENTION

The above-mentioned problems of current systems are addressed by embodiments of the present invention and will be understood by reading and studying the following specification. The following summaries of embodiments are made by way of example and not by way of limitation. The summaries may include more or less elements provided in the claims and are merely provided to aid the reader in understanding some of the aspects of the invention.

In one embodiment, a laryngoscope blade is provided. The blade includes a base, a relatively straight main blade portion and a distal tip. The relatively straight main blade portion has a length that extends from the base. The distal tip has a length that extends from the main blade portion. The distal tip further has a width that extends out beyond the width of the main blade in a select direction. The distal tip further yet has a bend at a select location about its length.

In another embodiment, another laryngoscope blade is provided. The blade includes a base, a relatively straight main blade portion and a distal tip. The relatively straight main blade portion has a length that extends from the base. The distal tip has a length that extends from the main blade portion. The distal tip further has a width that extends out beyond the width of the main blade in a select direction. Moreover, the length of the distal tip is longer than the length of the main blade portion.

In yet another embodiment, still another laryngoscope blade is provided. The blade includes a base, a relatively straight main blade portion and a distal tip. The relatively straight main blade portion has a length extending from the base. The distal tip has a length extending from the main blade portion. The distal tip has a width that extends out beyond a width of the main blade in a select direction. The distal tip has a distal end and a proximal end that define the length of the distal tip. Moreover, the proximal end of the distal tip has a wider width than the distal end of the distal tip.

In still another embodiment, a laryngoscope blade is provided. The laryngoscope blade includes a base and a blade. The base has a handle connector portion that is adapted to coupled a handle to the base. The blade has a length defined by a distal end and a proximal end. The proximal end is coupled to the base. The blade is generally straight throughout its length with a bend at a select angle near the distal end. The bend causes the distal end of the blade to be positioned in a general direction that the handle connector portion extends from the base. The distal end has a relatively straight portion that is generally perpendicular to an axis along the length of the blade. The distal end further has first and second curved edges. Moreover, the distal tip also has a slight curve along its width.

BRIEF DESCRIPTION OF THE DRAWINGS

The present invention can be more easily understood and further advantages and uses thereof more readily apparent, when considered in view of the description of the preferred embodiments and the following figures in which.

In accordance with common practice, the various described features are not drawn to scale but are drawn to emphasize specific features relevant to the present invention. Reference characters denote like elements throughout Figures and text.

DETAILED DESCRIPTION

In the following detailed description, reference is made to the accompanying drawings, which form a part hereof, and in which is shown by way of illustration specific embodiments in which the inventions may be practiced. These embodiments are described in sufficient detail to enable those skilled in the art to practice the invention, and it is to be understood that other embodiments may be utilized and that logical, mechanical and electrical changes may be made without departing from the spirit and scope of the present invention. The following detailed description is, therefore, not to be taken in a limiting sense, and the scope of the present invention is defined only by the claims and equivalents thereof.

Embodiments of the present invention provide an improved laryngoscope blade that is effective and versatile. The laryngoscope blade's design allows for it to be used to either move the entire connecting tissue superior to the epiglottis of a patient to expose the aditus of the larynx or engage the epiglottis to expose the aditus of the larynx. Hence, the present blade can be used in place of the two traditional types of blades. Moreover, the blade has added maneuverability and provides better visualization than traditional types of blade.

Figure 1:
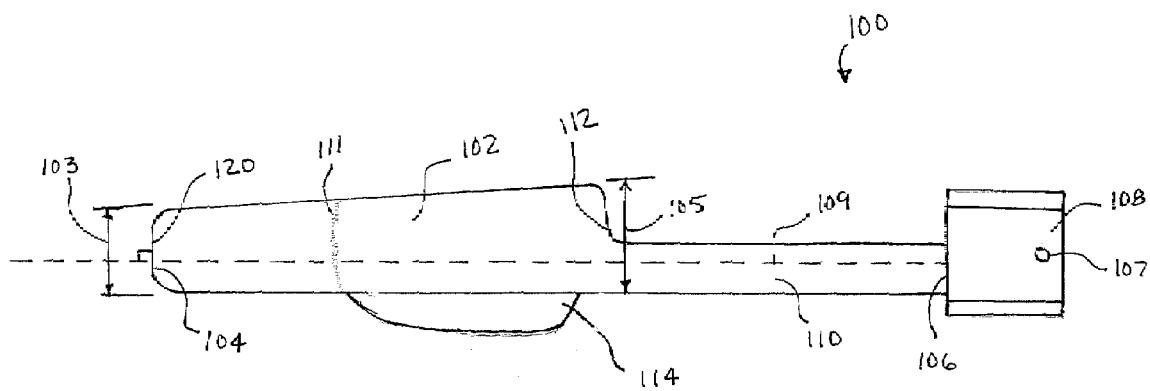
FIG. 1 is a top view of a laryngoscope blade of one embodiment of the present invention.

Referring to FIG. 1, a top view of one embodiment of a blade 100 of the present invention is illustrated. The blade 100 includes a base 108 that is designed to be coupled to a laryngoscope handle via handle connector portion 131(shown in FIG. 2). Illustrated on the base 108 is a light port 107 designed to direct light from a light source in the handle(not shown) to a light fiber coupled to the blade 100. The blade 100 further includes a relatively straight mid or main blade portion 110 that extends by a length from the base 108. A distal tip 102 further extends by a length from the main blade portion 110. As illustrated, the distal tip 102 is flared wider than the main blade portion 110. That is, the distal tip 102 has a width that is wider than the width of the main blade portion 110. This provides added maneuverability. The distal tip 102 in this embodiment has a shape that provides improved control of the epiglottis as well as an improved visual pathway to the aditus of the larynx by providing added control over tissue around the epiglottis. As illustrated, the distal tip has a first width 103 at the distal end 104 and a second width 105 at a proximal end 112 of the distal tip 102. The first width 103 is less than the second width 105 in this embodiment. In one embodiment, the length of the distal tip 102 is longer than the main blade portion 110.

Also illustrated in FIG. 1, is an axis 109 along the length of the blade 100. In one embodiment, the distal end 104 includes a relatively straight section (or portion) 120 that is generally perpendicular to axis 109. The distal tip 102 also has a bend 111 along its length in one embodiment. Further illustrated in FIG. 1, is a second tongue plate 114 that is designed to engage and move a patent's tongue out of the way when in use. As illustrated, the distal tip 102 extends out in width from the main blade portion 110 in a direction that is opposite of the second tongue plate 114. Further illustrated in FIG. 1 is a proximal end 106 of the main blade portion 110 that extends from the base 108.

Figure 2A:
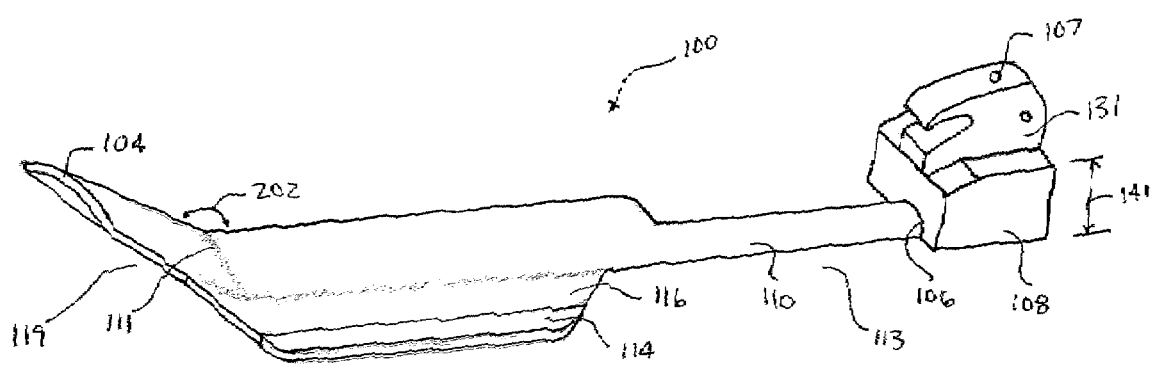
FIG. 2A is a side perspective view of the laryngoscope blade of FIG. 1.
Figure 2B:
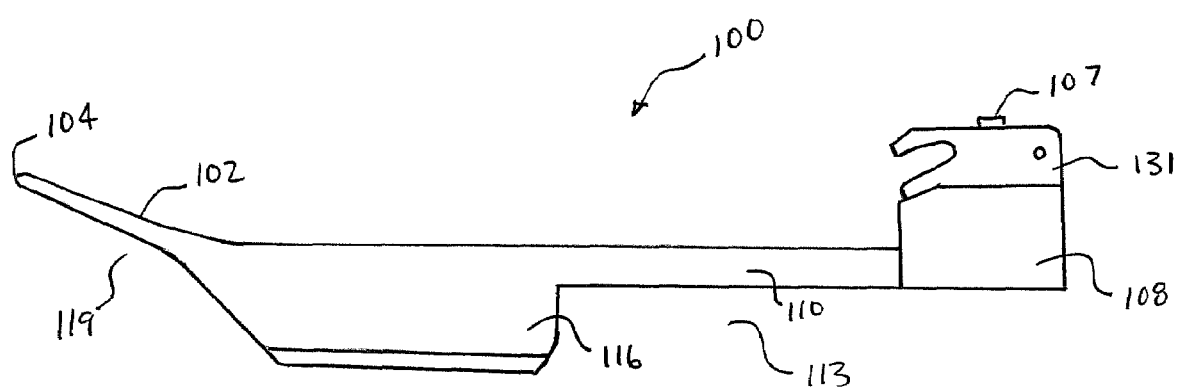
FIG. 2B is a side view of the laryngoscope blade of FIG. 1.

Referring to FIG. 2A a side perspective view of the laryngoscope blade of FIG. 1 is illustrated. As illustrated, the bend 111 is at a select length along the distal tip 102 at a select angle 202. The bend causes the distal end 104 to extend in the general direction as a handle connector portion 131 of the base. This bend 111 along with a cutout section 113 provides the blade with added maneuverability. In particular, cutout section 113 (or proximal cutout section) provides added maneuverability around a patent's teeth when in use. As part of the cutout section 113, neither a first tongue displacement plate 116 nor the main blade portion 110 at the proximal end 106 extend below a height 141 of the base 108 in this embodiment.

The first tongue displacement plate 116 extends from the distal tip 102 at approximately a 90° angle. In one embodiment, the first tongue displacement plate 116 further extends from a portion of the main blade portion 110 next to the distal tip 102. As illustrated, the second tongue displacement plate 114 extends from the first tongue displacement plate 116. In the embodiment of FIG. 2A, the second tongue displacement plate 114 extends from the first tongue displacement plate 116 at approximately a 90° angle in a direction opposite the direction the distal tip 102 extends wider than the main blade portion 110. In the embodiment of FIG. 2A, the first tongue displacement plate 116 has a cutout section 119 (or distal cutout section 119) near the distal end 104 of the blade 100. This cutout section 119 provides better visibility when the blade 100 is in use. The cutout section 119 is further illustrated in FIG. 2B.

Figure 3:
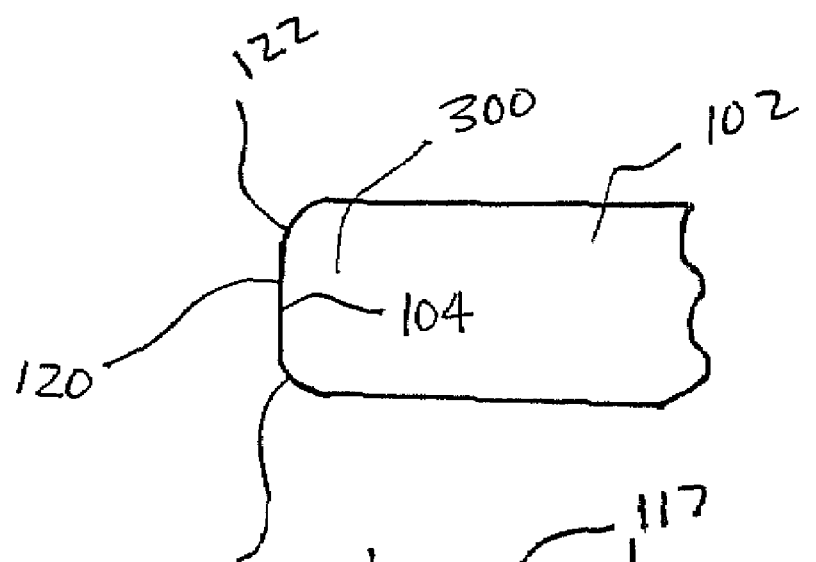
FIG. 3 is a top view of a partial distal tip of the laryngoscope blade of the present invention.
Figure 4:
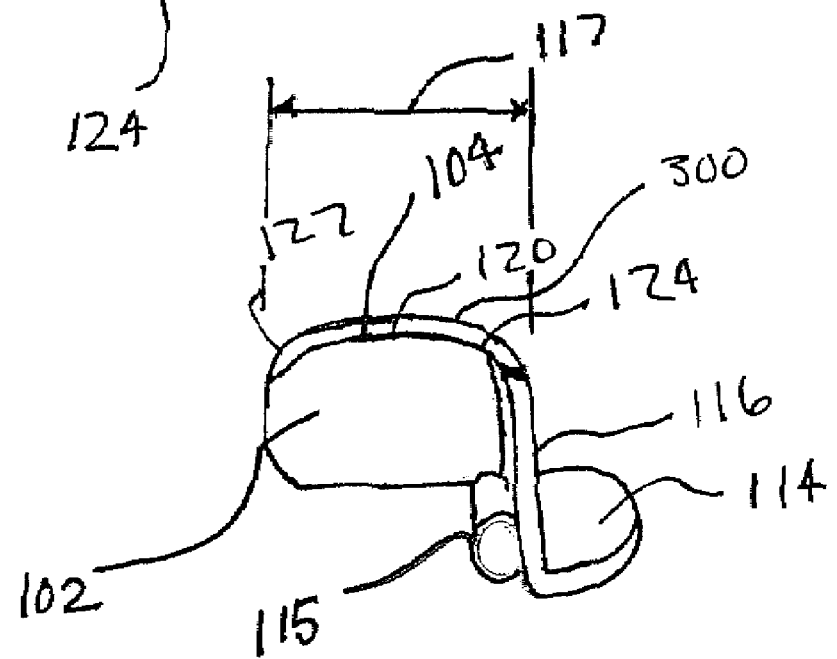
FIG. 4 is a front view of a distal end of a laryngoscope blade of the present invention.

In one embodiment of the present invention, the distal tip 104 of the blade is designed so that it can either be used to lift up the epiglottis or engage the connecting tissue superior to the epiglottis to view the adits of the larynx. Referring to FIG. 3, at top partial view of the distal tip 102 of one embodiment of the present invention is illustrated. As illustrated, the distal end 104 of the distal tip includes the relatively straight portion 120 that is generally perpendicular to the axis 113 along the length of the blade as illustrated in FIG. 1. The distal end 104 further includes curved edges 122 and 124. The curved edges 122 and 124 are of a select radius. In one embodiment, the radius of curve edge 122 and curve edge 124 are different. In another embodiment the radius of the curved edges are the same. FIG. 4 illustrates a front view of the blade. As illustrated, the distal tip 102 has a slight curve (or radius) along its width 117 at its distal end 104. The curve along its width forms a slight arch in a top surface 300 (engaging surface 300) of the blade 100 at the distal end 104. Also illustrated in FIG. 4 are the first tongue plate 116, the second tongue plate 114 and a light 115.

Figure 5:
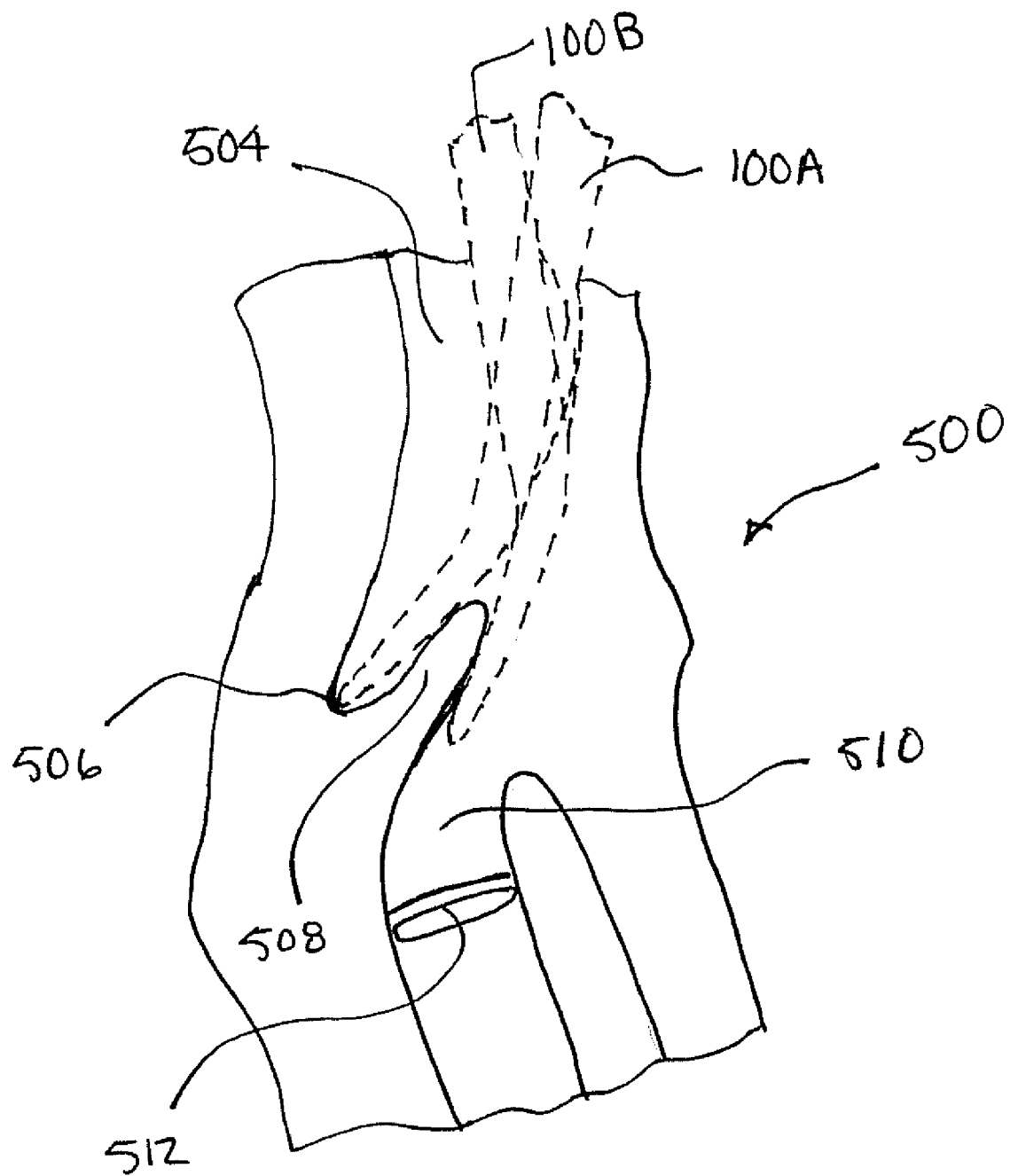
FIG. 5 is a cross-sectional side view of a patient's throat anatomy and laryngoscope blade tips of the present invention illustrating the multipurpose design.

The design of the distal tip 102 along with other features of the laryngoscope blade 100 allow the blade 100 to be used to either move the connecting tissue superior to the epiglottis or the epiglottis itself. Referring to FIG. 5, this is further illustrated. FIG. 5 is a cross-sectional side view of a patient's throat anatomy 500 and laryngoscope blade tips 100A and 100B of the present invention illustrating the multipurpose design. As illustrated, the throat anatomy 500 includes an oral cavity 504, connecting tissue superior to epiglottis 506, epiglottis 508, aditus of larynx 510 and the vocal cords 512. Blade 100A is illustrated as engaging the connecting tissue superior to the epiglottis 506 to move the epiglottis 508 in anterior direction to expose the aditus of larynx 510. The relatively straight portion 120 of the distal end 104 of the blade tip 102 along with the cutout section 113 and bend in the distal tip 102 of the blade 100 allows this maneuver. The use of blade 100B to engage and move the epiglottis is also illustrated in FIG. 5. The curved edges 122 and 124 of the distal end 104 of the distal tip 102 along with the slight curve along the width of the distal end 104 allow this maneuver. In particular, the shape of the distal end 104 is designed to effectively engage the naturally shape of the epiglottis 508.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention. Therefore, it is manifestly intended that this invention be limited only by the claims and the equivalents thereof.

The invention claimed is:
1. A laryngoscope blade, the blade comprising:
 a base having a base height extending between opposing base ends, one base end of the base configured and arranged to connect a handle thereto, the base further having a base width extending across a base side, the base width being generally in a perpendicular orientation with respect to the base height;
 a relatively straight main blade portion having a length that extends from the base side of the base, the main blade portion further having a main blade width, the main blade width extending in the same direction as the base width, the main blade further having a main blade height, the main blade height extending in the same direction as the base height; and
 a distal tip integral with the main blade portion having a length that extends from the main blade portion, the distal tip further having a distal tip width flared wider than the main blade width of the main blade portion in only one select direction, the distal tip further yet having a bend at a select location about its length.
2. The blade of claim 1 further comprising:
 the distal tip further having a distal end and a proximal end that define the length of the distal tip, the proximal end of the distal tip having a width that is wider than the width of the distal end of the distal tip.

3. The blade of claim 1, further comprising:
the distal tip having a distal end, the distal end having a relatively straight portion that is generally perpendicular to an axis along the length of the relatively straight main blade portion, the distal end further having first and second curved edges.

4. The blade of claim 1, further comprising:
the main blade portion having a cutout section adapted to allow added maneuverability about a patient's teeth when in use, wherein the main blade portion is positioned between the opposing base ends.

5. The blade of claim 1 further comprising:
a first tongue displacement plate extending from at least one of the distal tip and a portion of the main blade portion at generally a 90° angle, further wherein the first tongue displacement plate extends from the at least one of the distal tip and a portion of the main blade portion opposite the select direction in which the width of the distal tip extends out beyond the width of the main blade portion; and
a second tongue displacement plate extending from the first tongue displacement plate at approximately a 90° angle in a direction away from the distal tip.

6. The blade of claim 5, wherein the first tongue displacement plate has a cutout section proximate the distal tip that decreases the height of the distal tip.

7. A laryngoscope blade, the blade comprising:
a base having a base height extending between opposing base ends, one base end of the base configured and arranged to connect a handle thereto, the base further having a base width extending across a base side, the base width being generally in a perpendicular orientation with respect to the base height;
a relatively straight main blade portion having a length that extends from the base, the main blade portion further having a width that extends in the same direction as the base width; and
a distal tip integral with the main blade portion having a length that extends from the main blade portion, the distal tip further having a width flared wider than a width of the main blade in only one select direction, the length of the distal tip being longer than the length of the main blade portion.

8. The blade of claim 7, wherein the distal tip has a bend at a select location about its length.

9. The blade of claim 7, further comprising:
the distal tip further having a distal end and a proximal end defining the length of the distal tip, the proximal end having a width that is wider than the width of the distal end.

10. The blade of claim 7, further comprising:
the distal tip having a distal end, the distal end having a relatively straight portion that is generally perpendicular to an axis formed by length of the relatively straight main portion, the distal end further having first and second curved edges.

11. A laryngoscope blade, the blade comprising:
a base having a base height extending between opposing base ends, one base end of the base configured and arranged to connect a handle thereto, the base further having a base width extending across a base side, the base width being generally in a perpendicular orientation with respect to the base height;
a relatively straight main blade portion having a length extending from the base side of the base; and
a distal tip integral with the main blade portion having a length extending from the main blade portion, the distal tip having a width that is flared wider than the width of the main blade in only one select direction, the distal tip having a distal end and a proximal end that define the length of the distal tip, the proximal end of the distal tip having a wider width than the distal end of the distal tip.

12. The blade of claim 11, wherein the distal tip has a bend at a select location about its length.

13. The blade of claim 11, further comprising:
the distal tip having a distal end, the distal end having a relatively straight portion that is generally perpendicular to an axis along the length of the relatively straight main portion and first and second curved edges.

14. The blade of claim 11, wherein the length of the distal tip is longer than the length of the main blade portion.

15. A laryngoscope blade, the laryngoscope blade comprising:
a base having a handle connector portion adapted to couple a handle to the base, the base further having a base height extending between opposing base ends, one base end of the base configured and arranged to connect the handle thereto, the base further having a base width extending across a base side, the base width being generally in a perpendicular orientation with respect to the base height;
a blade having a length defined by a distal end and a proximal end, the proximal end coupled to the base, the blade having a main blade portion extending from the base and a distal tip portion integral with the main blade portion extending from the main blade portion, the main blade portion having a main blade width that extends in the same direction as the base width, the distal tip flared out wider than the main blade width in only one select direction; and
a tongue displacement member that extends from the distal tip portion of the blade along a length of the distal tip portion, the tongue displacement tip configured and arranged to displace a tongue when in use.

16. The laryngoscope blade of claim 15, wherein the tongue displacement member includes a first tongue displacement plate and a second tongue displacement plate.

17. The laryngoscope blade of claim 16, wherein the first tongue displacement plate extends from the blade along the length of the distal tip portion at generally a right angle.

18. The laryngoscope blade of claim 17, wherein the second tongue displacement plate extends generally perpendicular from the first tongue displacement plate in a direction such that the second tongue displacement plate extends away from the blade in a direction that is opposite the only one select direction in which the distal tip portion flares wider than the blade.

19. The laryngoscope blade of claim 15, wherein the blade being generally straight throughout its length with a bend at a select angle along a length of the distal tip portion, the bend causing the distal end of the blade to be positioned in a general direction that the handle connector portion extends from the base.

20. The laryngoscope blade of claim 15, wherein the length of the distal tip portion is defined by a proximal end and a distal end, the proximal end extending from the main blade portion, the proximal end of the distal tip having a width that is wider than the width of the distal end.

* * * * *